United States Patent [19]

Spiess et al.

[11] Patent Number: 4,859,787
[45] Date of Patent: Aug. 22, 1989

[54] PROCESS FOR THE PREPARATION OF DIALKYLDITHIOCARBAMATES OF MULTIVALENT METALS

[75] Inventors: Wolfram Spiess; Rolf Himmelreich, both of Grünstadt, Fed. Rep. of Germany

[73] Assignee: C. F. Spiess & Sohn GmbH & Co., Kleinkarlbach, Fed. Rep. of Germany

[21] Appl. No.: 185,174

[22] Filed: Apr. 22, 1988

[30] Foreign Application Priority Data

Apr. 30, 1987 [DE] Fed. Rep. of Germany ....... 3714436

[51] Int. Cl.$^4$ ........................................... C07C 155/06
[52] U.S. Cl. .................................................... 558/235
[58] Field of Search ........................................ 558/235

[56] References Cited

U.S. PATENT DOCUMENTS 4,645,661 2/1987 Schonbaum ..................... 558/235

Primary Examiner—John M. Ford
Assistant Examiner—Robert C. Whittenbaugh
Attorney, Agent, or Firm—Sprung Horn Kramer & Woods

[57] ABSTRACT

A direct method of preparing dialkyl-dithiocarbamates of multivalent metals by reacting the oxide of a multivalent metal with a secondary amine and carbon disulfide while simultaneously heating to 50°–95° C. and removing the so-formed water of the reaction.

Suitable metal oxides are preferably lead oxide, zinc oxide, copper(II)oxide, iron(III)oxide, nickel(III)oxide, antimony(III)oxide and manganese dioxide. The reaction is preferably conducted in a solvent for the metal-dialkyl-dithiocarbamate which forms an azeotrope with water in order to remove the water of the reaction with the solvent.

8 Claims, No Drawings

PROCESS FOR THE PREPARATION OF DIALKYLDITHIOCARBAMATES OF MULTIVALENT METALS

This application relates to a new process for the preparation of dialkyl-dithiocarbamates of multivalent metals. They are usually prepared by a double reaction of dialkyl-dithiocarbamates of the alkali metals, the ammonium or the dialkyl ammonium compounds with metal salts. See Elsevier Monographs "The Dithiocarbamates and related Compounds" by Thorn and Ludwig (1962).

It was found now that the preparation is also possible by direct reaction of secondary amines with carbon disulfide and multivalent oxides in stoichiometric amounts. The mixture has to be heated thereby, preferably to temperatures of from 50° to 95° C., whereby an amount of water corresponding to the oxygen atoms of the metal oxide is formed.

The preparation of the metal-dialkyl-dithiocarbamates of the invention proceeds according to the following reaction mechanism:

For bivalent metals:

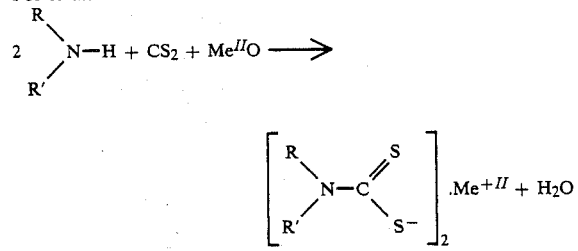

For trivalent metals:

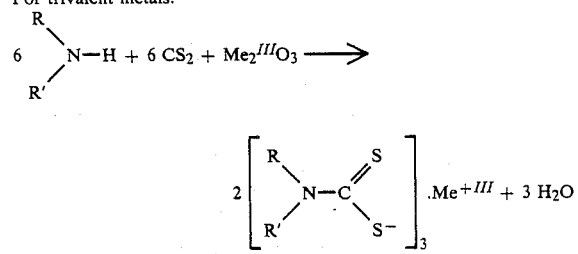

For tetravalent metals:

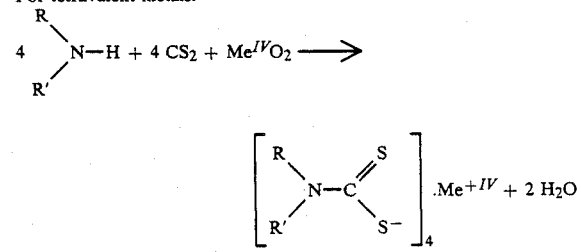

R and R' in the general formula represent the same or different straight- or branched-chain saturated or unsaturated hydrocarbon or cycloalkyl groups having from 1 to 13 carbon atoms.

Examples of bivalent metal oxides $Me^{II}O$ are CuO, ZnO and PbO.

Examples of oxides of trivalent metals $Me_2^{III}O_3$ are $Fe_2O_3$, $Ni_2O_3$ and $Sb_2O_3$.

An example of an oxide of a tetravalent metal $Me^{IV}O_2$ which according to the process of the invention can be directly converted into a dialkyl-dithiocarbamate is manganese dioxide. If the metal-dialkyl-dithiocarbamate is liquid under the reaction conditions, i.e. not yet crystallized, the reaction may be carried out without a solvent. The water of the reaction will in that case be distilled off in vacuo, basically after termination of the reaction but preferably to the extent as it is formed during the reaction.

The process of the invention is preferably conducted in a solvent for the metal-dialkyl-dithiocarbamate. It is useful to select a solvent that forms an azeotrope with water. The reaction can then be conducted at the boiling point of the azeotrope and the water of the reaction is removed as it is formed during the reaction. Suitable solvents to this end are benzene, toluene, cyclohexane and ethers of higher boiling points, such as diisopropyl ether or butyl ethyl ether, as well as alkanes having from 6 to 8 carbon atoms, straight- or branched-chain, e.g. n-hexane, n-heptane, n-octane or isooctane.

The process is carried out, for example, as follows: The solvent which forms an azeotrope with water is placed in a vessel. A secondary amine and the metal oxide are then added thereto. The carbon disulfide is subsequently added drop by drop while it is mechanically stirred. The mixture is further stirred up to three hours and then heated to its boiling point at reflux provided with water separator. The reaction is terminated when the calculated amount of water is separated. This is the case after 1 to 6 hours. The solution is thereafter filtered and the solvent is distilled off from the filtrate. The residue is preferably recrystallized from a suitable solvent, such as lower alcohols, ethers or acetone. It can however also be directly dissolved in a mineral oil. For example, 50%-solutions of the active ingredient may be thus prepared; they are directly marketable products and are used as additives and antioxidants in hydraulic and transmission lubricants. It is, therefore, recommendable to conduct the process directly in a high-boiling mineral oil which may have an aromatic component of from 1 to 15 percent, such as, for example, raffinates, technical white oils or spindle oils which start to boil at 250° C. at 760 Torr. Instead of mineral oils one can also use high-boiling ester waxes or fatty acid esters.

With mineral oil as solvent, the procedure may be conducted, for example, as follows:

The mineral oil is placed in a vessel and the finely powdered metal oxide and the secondary amine are added with stirring. After adding the carbon disulfide drop by drop and an after-reaction time, the mixture is heated at reflux to 50°–95° C. for 1–12 hours while it is mechanically stirred. The so-formed water is subsequently distilled off in vacuo. The heating may also be conducted in vacuo, the water formed being simultaneously distilled off, which shortens the reaction time. The remaining solution is filtered to directly yield a relatively concentrated solution of the active ingredient in mineral oil.

In preparing the metal-dialkyl-dithiocarbamates of this invention, a stoichiometric excess of metal oxide of from 10 to 100 percent is generally used. Some metal oxides, such as lead oxide and zinc oxide form small amounts of metal sulfides during the reaction.

The metal oxide residues which might possibly contain sulfide can be used again in further runs. When using a 100 percent excess of zinc oxide, the zinc sulfide content was increased from, for example, 6.6 percent in the residue of the first run to 25.6 percent after the 8th run and then remained constant.

Due to its high volatility, the carbon disulfide is at best used in a stoichiometric excess of from 5 to 20 percent.

The preparation of the metal-dialkyl-dithiocarbamates of the present invention is described in detail in the following examples:

EXAMPLE 1

Lead-bis-(diamyl-dithiocarbamate)

111.5 g lead(II)oxide (Merck) are added to 300 g Solvent Raffinat HR 22 (Lehmann und Voss). 157 g diamyl amine (Hoechst) are added thereto. 64 ml of carbon disulfide are subsequently added drop by drop in the course of 30 minutes while mechanically stirring at reflux. The mixture is stirred for further 45 minutes. It is subsequently heated with downstream condenser in water-jet vacuum for 2½ hours to 90° C. The water of the reaction formed thereby is distilled off. 2 g of filtering adjuvants (diatomaceous earth) (Seitz) are subsequently admixed thereto and the solution is sucked off while it is hot. 600 g of an amber-yellow oil is obtained having a content of 52.1 percent.

The analysis of the here described dithiocarbamates is carried out via a nitrogen determination or via a cleavage of the carbon disulfide followed by a quantitative analysis.

EXAMPLE 2

Lead-bis-(diisononyl-dithiocarbamate)

1125 lead oxide, 3100 g Solvent Raffinat HR 22 and 2690 g diisononyl amine (Hoechst) are placed in a 10 liter three-necked flask. 640 ml carbon disulfide are then added drop by drop with mechanical stirring at reflux in the course of one hour. The mixture is stirred for further 90 minutes and is subsequently heated for 9 hours in vacuo to 90° C. After adding 10 g of filtering adjuvant, it is sucked off with a suction filter heated with low-pressure steam. 6228 g of a light amber colored oil are obtained, having a content of 55.6%. 522 g Solvent Raffinat HR 22 are additionally added thereto to yield 6750 g oil containing 51% of the lead salt.

EXAMPLE 3

Zinc-bis-(diamyl-dithiocarbamate)

100 g zinc oxide are added to 278.7 g Deumos Spezial Raffinat 32 (Texaco) and 196.3 g diamyl amine. Within 30 minutes, 80 ml carbon disulfide are added thereto drop by drop with mechanical stirring at reflux. The mixture is stirred further for another 30 minutes. It is subsequently heated in a water bath for 3 hours to 95° C. The so-obtained water of the reaction is thereafter distilled off in vacuo in a rotary evaporator. The insolubles are sucked off, 575 g of a light yellow oil are obtained, having a content of 52.8%.

EXAMPLE 4

Zinc-bis-(isobutyl-isooctyl-dithiocarbamate)

82 g zinc oxide are added to 295 g Solvent Raffinat HR 22 and 185 g isobutyl-isooctyl amine (Hoechst). 64 ml carbon disulfide are then added thereto drop by drop with mechanical stirring at reflux in the course of 30 minutes. The mixture is further stirred for another 30 minutes followed by heating for 5 hours in a water bath to 95° C. The so-formed water is distilled off in vacuo in a rotary evaporator. It is then sucked off while it is hot after adding 3 g diatomaceous earth, 503 g of a light yellow oil are obtained, having a content of 51.1%.

EXAMPLE 5

Copper-bis-(diamyl-dithiocarbamate)

160 g Copper oxide are added to 500 g Solvent Raffinat HR 22 and 314 diamyl amine. 128 ml carbon disulfide are then added thereto drop by drop with mechanical stirring at reflux in the course of 30 minutes. The mixture is heated for 9 hours to 95° C. The so-obtained water is distilled off in vacuo in a rotary evaporator. The solution is subsequently sucked off. One obtains 952 g of a brown viscous liquid having a content of 50.2%.

EXAMPLE 6

Iron-tris-(diamyl-dithiocarbamate)

100 g iron(III) oxide are added to 475 g Solvent Raffinat HR 22 and 314 g diamyl amine. 128 ml carbon disulfide are added thereto drop by drop with mechanical stirring at reflux in the course of 30 minutes. The mixture is heated for 9 hours in a water bath to 95° C. The so-formed water is subsequently distilled off in vacuo in a rotary evaporator at a bath temperature of 90° C. The insolubles are then sucked off in the hot condition. The iron salt crystallizes upon cooling. The precipitate is sucked off. The residue is recrystallized from isopropanol to give 388 g of a black brilliant crystalline substance having a melting point of 85° C. The product has a purity of 98.1%.

EXAMPLE 7

Nickel-tris-(di-2-ethylhexyl-dithiocarbamate)

20 g NIckel(III)oxide ($Ni_2O_3$) are added to 121 g di-2-ethylhexyl amine and 150 ml benzene. 32 ml carbon disulfide are added thereto drop by drop in the course of 20 minutes with mechanical stirring at reflux. The mixture is further stirred for another 2 hours. The mixture is subsequently heated to its boiling point at reflux provided with water separator. The reaction is terminated when 4.5 ml water are separated. This is the case after 3 hours. The insolubles are sucked off in the hot condition. Benzene is distilled off from the filtrate. The residue is dried for 45 minutes in vacuo at 90° C. One obtains 130 g of a black-green oil which crystallizes upon intense cooling (Fp 21° C.). The product has a purity of 95.6%.

EXAMPLE 8

Antimony-tris-(diamyl-dithiocarbamate)

537 kg spindle oil Raffinat ET 22 Iso (Ölwerke Julius Schindler, Hamburg), 90 kg antimony oxide ($Sb_2O_3$) and 263 kg diamyl amine are mixed in a 2000 liter enameled vessel. 136 kg carbon disulfide are added thereto with stirring in the course of 45 minutes. The mixture is further stirred for another hour. It is subsequently heated in vacuo and the water of the reaction is distilled off thereby. The main reaction takes place at 55° C. The distilled amount of water begins to decrease after 2 hours and the temperature rises further. The mixture is heated for another 3 hours to 90°–93° C. 2.5 kg filtering adjuvant (diatomaceous earth) are subsequently added thereto followed by sucking off through a filter press in the hot condition. One obtains 957 kg of an amber-yellow oil having a purity of 45.2%. The yield is 97.7% of the theoretical amount.

EXAMPLE 9

Manganese-tetra-(di-2-ethylhexyl-dithiocarbamate)

52 g manganese dioxide (85-90%) are added to 482 g di-2-ethylhexyl amine. 128 ml carbon disulfide are added thereto drop by drop with mechanical stirring at reflux in the course of 40 minutes. The mixture is stirred for another 3 hours followed by heating to 95° C. in a rotary evaporator in vacuo. The reaction time is 10 hours. The insolubles are subsequently sucked off by a vapor-heated suction filter. 573 g of a black-brownish oil are obtained having a purity of 94.34%. The yield is 86.6% of the theoretical amount.

It will be appreciated that the instant specification and claims are set forth by way of illustration and not limitation, and that various modifications and changes may be made without departing from the spirit and scope of the present invention.

What is claimed is:

1. A process for the preparation of a multivalent metal salt of a dialkyl-dithiocarbamate comprising reacting the oxide of a multivalent metal selected from the group consisting of lead oxide, zinc oxide, copper(II)oxide, iron(III)oxide, nickel(III)oxide, antimony(III)oxide and manganese dioxide, with a secondary amine of the formula

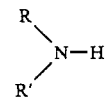

wherein R and R' represent the same or different straight or branched-chained saturated or unsaturated hydrocarbon or cycloalkyl groups having from 1 to 13 carbon atoms and carbon disulfide and removing the formed water of reaction.

2. A process according to claim 1, wherein the reaction is conducted in a solvent for the metal-dialkyldithiocarbamate.

3. A process according to claim 2, wherein the solvent forms an azeotrope with water and the water of the reaction is removed with the solvent.

4. A process according to claim 2, wherein the solvent is selected from the group consisting of spindle oil, white oil, refinery oil, liquid ester waxes and liquid fatty acid esters.

5. A process according to claim 4, wherein the water of the reaction is distilled off in vacuo during the reaction.

6. A process according to claim 1, wherein the metal oxide is used in a stoichiometric excess of from 10 to 100 percent.

7. A process according to claim 1, wherein the carbon disulfide is used in a stoichiometric excess of from 5 to 20 percent.

8. A process according to claim 1, wherein the reaction is conducted at a temperature of from 50° to 95° C.

* * * * *